(12) United States Patent
Tommasi (10) Patent No.: US 11,918,719 B2
(45) Date of Patent: Mar. 5, 2024

(54) BLOOD PROCESSING UNIT (BPU) WITH COUNTERCURRENT BLOOD/WATER FLOW PATHS IN THE HEAT EXCHANGER (HEX)

(71) Applicant: Sorin Group Italia S.r.l., Milan (IT)

(72) Inventor: Gabriele Tommasi, Cavezzo (IT)

(73) Assignee: Sorin Group Italia S.r.l., Milan (IT)

( * ) Notice: Subject to any disclaimer, the term of this patent is extended or adjusted under 35 U.S.C. 154(b) by 898 days.

(21) Appl. No.: 16/755,107

(22) PCT Filed: Oct. 10, 2017

(86) PCT No.: PCT/IB2017/056252
§ 371 (c)(1),
(2) Date: Apr. 9, 2020

(87) PCT Pub. No.: WO2019/073279
PCT Pub. Date: Apr. 18, 2019

(65) Prior Publication Data
US 2020/0237994 A1    Jul. 30, 2020

(51) Int. Cl.
*A61M 1/16* (2006.01)
*A61M 1/36* (2006.01)

(52) U.S. Cl.
CPC ........ *A61M 1/1698* (2013.01); *A61M 1/3623* (2022.05); *A61M 1/3666* (2013.01); *A61M 2205/366* (2013.01); *A61M 2206/14* (2013.01); *A61M 2206/20* (2013.01)

(58) Field of Classification Search
CPC .............. A61M 1/1698; A61M 1/3666; A61M 2205/36; A61M 2205/366; A61M 2206/14; A61M 2206/20
See application file for complete search history.

(56) References Cited

U.S. PATENT DOCUMENTS

| 8,394,049 B2 | 3/2013 | Reggiani et al. |
| 2002/0039543 A1 * | 4/2002 | Ikeda ................... B01D 63/021 604/6.14 |

FOREIGN PATENT DOCUMENTS

| EP | 2543403 A2 | 1/2013 |
| JP | 2016039995 A | 3/2016 |
| WO | 2015008327 A1 | 1/2015 |
| WO | 2015104725 A1 | 7/2015 |
| WO | WO-2015104725 A1 * | 7/2015 .......... A61M 1/1629 |
| WO | 2016181189 A1 | 11/2016 |

* cited by examiner

*Primary Examiner* — Benjamin J Klein (74) *Attorney, Agent, or Firm* — Seager, Tufte & Wickhem LLP (57) ABSTRACT

Described is a blood processing apparatus with a blood flow path and a heat exchanger fluid flow path overlapping the a heat exchanger chamber, in which the blood flows generally from a first end to a second end of the blood processing apparatus, and the heat exchanger fluid flows generally from the second end to the first end. Such "counter" or "countercurrent" flow improves heat transfer between the blood and the heat exchanger fluid. The blood processing apparatus includes a housing, a blood inlet, a heat exchanger fluid inlet and a heat exchanger fluid outlet, a heat exchanger core, a cylindrical shell having an annular shell aperture, a blood flow distributor, and a central chamber in fluid communication to a fluid flow distributor.

17 Claims, 9 Drawing Sheets

BLOOD PROCESSING UNIT (BPU) WITH COUNTERCURRENT BLOOD/WATER FLOW PATHS IN THE HEAT EXCHANGER (HEX)

CROSS REFERENCE TO RELATED APPLICATION

This application is a national stage application of PCT/IB2017/056252, filed Oct. 10, 2017, which is herein incorporated by reference in its entirety.

TECHNICAL FIELD

This disclosure pertains generally to blood processing units used in blood perfusion systems.

BACKGROUND

Blood perfusion entails encouraging blood flow through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen can be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

SUMMARY

Example 1 is a blood processing apparatus comprising: a housing having a first end and a second end; a blood inlet at the first end; a heat exchanger fluid inlet and a heat exchanger fluid outlet at the second end; a heat exchanger core situated in the housing; a cylindrical shell extending coaxially about the heat exchanger core; a blood flow distributor in fluid communication with the blood inlet near the first end and configured to direct blood from the blood inlet at the first end through the blood flow distributor to a heat exchanger chamber; a plurality of heat exchanger hollow fibers disposed in the heat exchanger chamber, the heat exchanger hollow fibers configured to direct heat exchanger fluid from the heat exchanger fluid inlet at the second end through the heat exchanger hollow fibers to a fluid flow distributor near the first end; and a central chamber disposed in the heat exchanger core and in fluid communication with the fluid flow distributor, the central chamber configured to direct heat exchanger fluid from the fluid flow distributor near the first end through the central chamber to the heat exchanger fluid outlet at the second end.

Example 2 is the blood processing apparatus of example 1, wherein the heat exchanger chamber is defined by an exterior of the heat exchanger core and an interior of the cylindrical shell.

Example 3 is the blood processing apparatus of example 1, wherein the cylindrical shell further includes an annular shell aperture near the second end and configured to direct blood from the heat exchanger chamber to an exterior of the cylindrical shell.

Example 4 is the blood processing apparatus of example 1, further comprising: an inlet chamber in fluid communication with the heat exchanger fluid inlet and the entirety of the heat exchanger hollow fibers near the second end.

Example 5 is the blood processing apparatus of example 1, further comprising: a post chamber in fluid communication with the entirety of the heat exchanger hollow fibers and the fluid flow distributor near the first end.

Example 6 is the blood processing apparatus of example 1, wherein the blood flow distributor and the fluid flow distributor are portions of a multi-flow distributor.

Example 7 is the blood processing apparatus of example 1, wherein the blood flow distributor defines a plurality of radially distributed blood distributing apertures equally spaced around a circumference of the blood flow distributor.

Example 8 is the blood processing apparatus of example 1, wherein the fluid flow distributor defines a plurality of radially distributed fluid distributing apertures equally spaced around a circumference of the fluid flow distributor.

Example 9 is the blood processing apparatus of example 1, wherein the blood flow distributor is disposed 5 percent to 35 percent of a length of the housing from the first end.

Example 10 is the blood processing apparatus of example 1, wherein the fluid flow distributor is disposed 5 percent to 35 percent of a length of the housing from the first end.

Example 11 is the blood processing apparatus of example 1, wherein the annular shell aperture is disposed 5 percent to 25 percent of a length of the housing apart from the second end.

Example 12 is a blood processing apparatus comprising: a housing having a first end and a second end; a blood inlet at the first end; heat exchanger fluid inlet and a heat exchanger fluid outlet at the second end; a heat exchanger core situated in the housing; a cylindrical shell extending coaxially about the heat exchanger core and includes an annular shell aperture near the second end; a blood flow distributor in fluid communication with the blood inlet near the first end and configured to direct blood from the blood inlet at the first end through the blood flow distributor to a heat exchanger chamber, and through the annular shell aperture to an exterior of the cylindrical shell near the second end; and a plurality of heat exchanger hollow fibers disposed in the heat exchanger chamber such that heat exchanger fluid flows from the heat exchanger fluid inlet through an inlet chamber to the entirety of the heat exchanger hollow fibers near the second end, and to a post chamber in fluid communication with the entirety of the heat exchanger hollow fibers near the first end.

Example 13 is the blood processing apparatus of example 12, further comprising: a fluid flow distributor in fluid communication with the post chamber.

Example 14 is the blood processing apparatus of example 12, wherein the heat exchanger chamber is defined by an exterior of the heat exchanger core and an interior of the cylindrical shell.

Example 15 is the blood processing apparatus of example 12, further comprising: a central chamber disposed in the heat exchanger core in fluid communication with the fluid flow distributor, the central chamber configured to direct heat exchanger fluid from the post chamber near the first end through the central chamber to the heat exchanger fluid outlet at the second end.

Example 16 is the blood processing apparatus of example 12, wherein the blood flow distributor defines a plurality of radially distributed blood distributing apertures equally spaced around a circumference of the blood flow distributor.

Example 17 is the blood processing apparatus of example 13, wherein the fluid flow distributor defines a plurality of radially distributed fluid distributing apertures equally spaced around a circumference of the fluid flow distributor.

Example 18 is a method of directing blood and heat exchanger fluid through a blood processing apparatus comprising: providing a blood processing apparatus having a housing having a first end and a second end, a blood inlet at the first end, a heat exchanger fluid inlet and a heat exchanger fluid outlet at the second end, a heat exchanger core situated in the housing, a cylindrical shell extending coaxially about the heat exchanger core, the cylindrical shell having an annular shell aperture disposed near the second end, a blood flow distributor in fluid communication with the blood inlet near the first end, a plurality of heat exchanger hollow fibers disposed about an exterior of the heat exchanger core, and disposed in a heat exchange chamber, and a central chamber disposed in the heat exchanger core in fluid communication to a fluid flow distributor; directing blood from the blood inlet at the first end through the blood flow distributor to the exterior of the heat exchanger core in the heat exchange chamber, and through the annular shell aperture near the second end; and directing heat exchanger fluid from the heat exchanger fluid inlet at the second end through the heat exchanger hollow fibers to a fluid flow distributor near the first end and to the central chamber and to the heat exchanger fluid outlet at the second end.

Example 19 is the method of directing blood and heat exchanger fluid of example 18, further comprising: directing heat exchanger fluid from the heat exchanger inlet through an inlet chamber to the entirety of the heat exchanger hollow fibers.

Example 20 is the method of directing blood and heat exchanger fluid of example 18, further comprising: directing heat exchanger fluid from the entirety of the heat exchanger hollow fibers through a post chamber to the fluid flow distributor.

DETAILED DESCRIPTION

Figure 1:
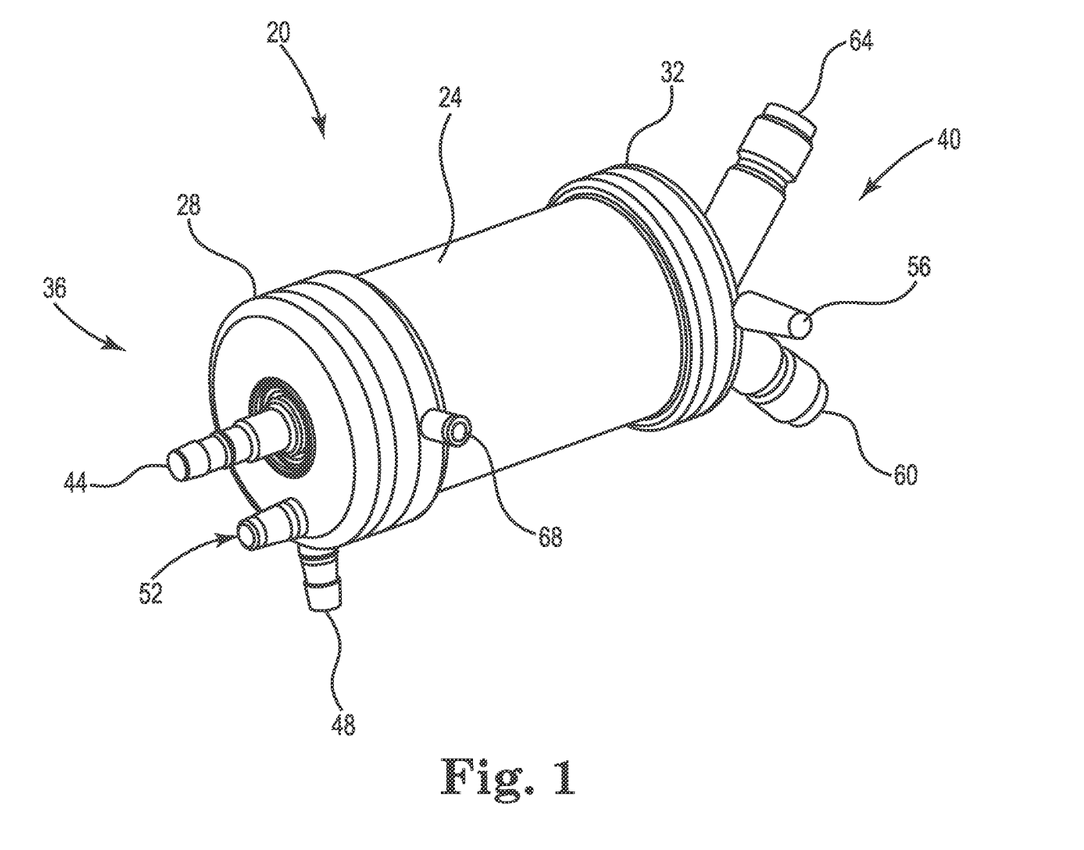
FIG. 1 is a diagram illustrating a blood processing apparatus, in accordance with various embodiments of the disclosure.

The disclosure pertains to a blood processing apparatus 20 (also referred to as an oxygenator). FIG. 1 is a diagram illustrating a blood processing apparatus 20, in accordance with various embodiments of the disclosure. The blood processing apparatus 20 includes a housing 24, a first end cap 28 that is secured to the housing 24 near a first end 36, and a second end cap 32 that is secured to the housing 24 near a second end 40. While the housing 24 is illustrated as largely cylindrical in shape, alternative embodiments include housing 24 of other cross-sectional shapes (e.g. triangular, squared, hexagonal).

As shown in FIG. 1, a blood inlet 44 extends into the housing 24 through the first end cap 28 and a blood outlet 48 positioned near the first end 36 on the housing 24. A gas inlet 52 is located on the first end cap 28 and a gas outlet 56 is located on the second end cap 32. A heat exchanger fluid inlet 60 and a heat exchanger fluid outlet 64 are located on the second end cap 32. The blood inlet 44 is concentrically positioned with the first end cap 28. The gas inlet 52 is a portion of the first end cap 28. The gas outlet 56 is a portion of the second end cap 32. The heat exchanger fluid inlet 60 and the heat exchanger fluid outlet 64 are portions of the second end cap 32. The blood processing apparatus 20 includes a purge port 68 configured to purge air bubbles trapped in the blood processing apparatus 20.

Figure 2:
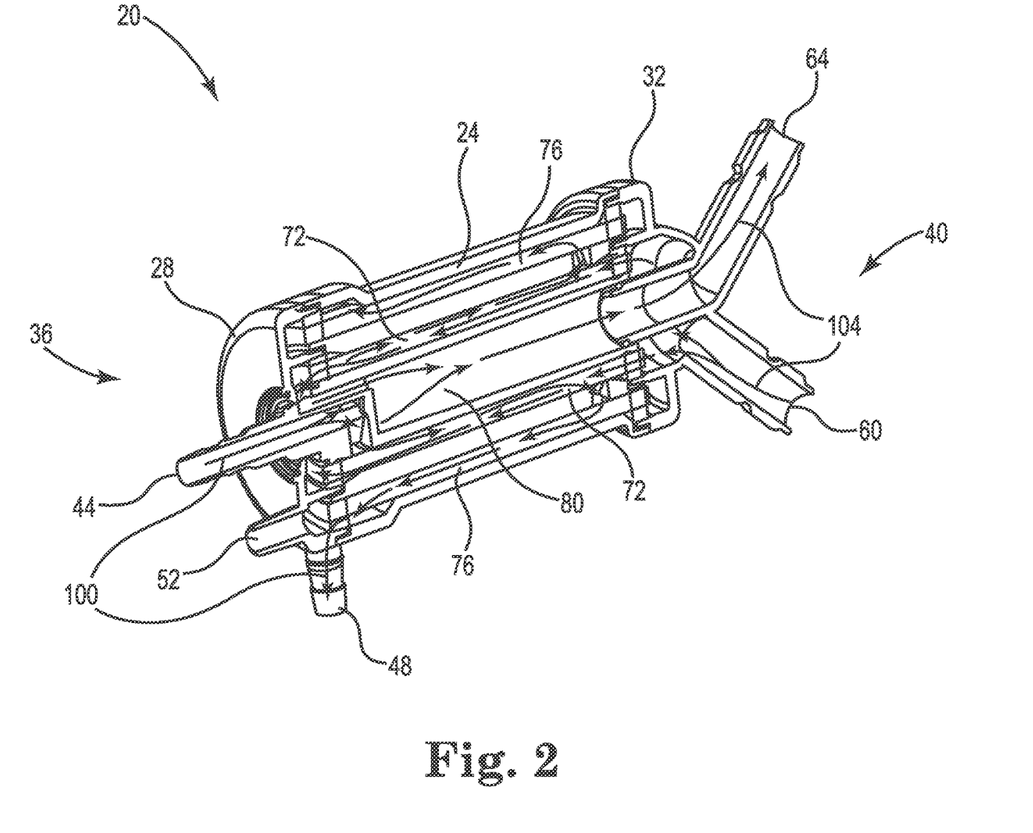
FIG. 2 is a cross-sectional diagram illustrating a blood processing apparatus, in accordance with various embodiments of the disclosure.

FIG. 2 is a cross-sectional diagram illustrating the blood processing apparatus, in accordance with various embodiments of the disclosure. As indicated in FIG. 2, the blood processing apparatus 20 includes one or more heat exchanger chamber(s) 72 and gas exchanger chamber(s) 76, located in the housing 24, and in between the first and second end caps 28, 32. During operation, blood flows from the blood inlet near the first end 36 generally to the second end 40 through the heat exchanger chamber 72, then from the second end 40 back to the first end 36 through the gas exchanger chamber 76, and exits the blood processing apparatus 20 from the blood outlet 48. As shown, heat exchanger fluid flows from the heat exchanger fluid inlet 60 near the second end 40 generally to the first end 36 through the heat exchanger chamber 72, then from the first end 36 back to the second end 40 through a central chamber 80, and exits the blood processing apparatus 20 from the heat exchanger fluid outlet 64. During operation, gas flows from the gas inlet 52 near the first end 36 generally to the second end 40 through the gas exchanger chamber 76 and exits the blood processing apparatus 20 from the gas outlet 56. The heat exchanger chamber 72 and the gas exchanger chamber 76 can be concentric.

As shown in FIG. 2, the blood flow path 100 and the heat exchanger fluid flow path 104 overlaps in the heat exchanger chamber 72, in which the blood flows generally from the first end 36 to the second end 40, and the heat exchanger fluid flows generally from the second end 40 to the first end 36. In other words, at least for some portion of the heat exchanger chamber 72, the blood and heat exchanger fluid flow in generally opposing directions. For brevity, this flow configuration will be referred to as "counter" or "countercurrent" flow in this disclosure. Note that improved heat transfer between the blood and the heat exchanger fluid is achieved through utilizing countercurrent flow in the heat exchanger chamber 72.

Figure 3:
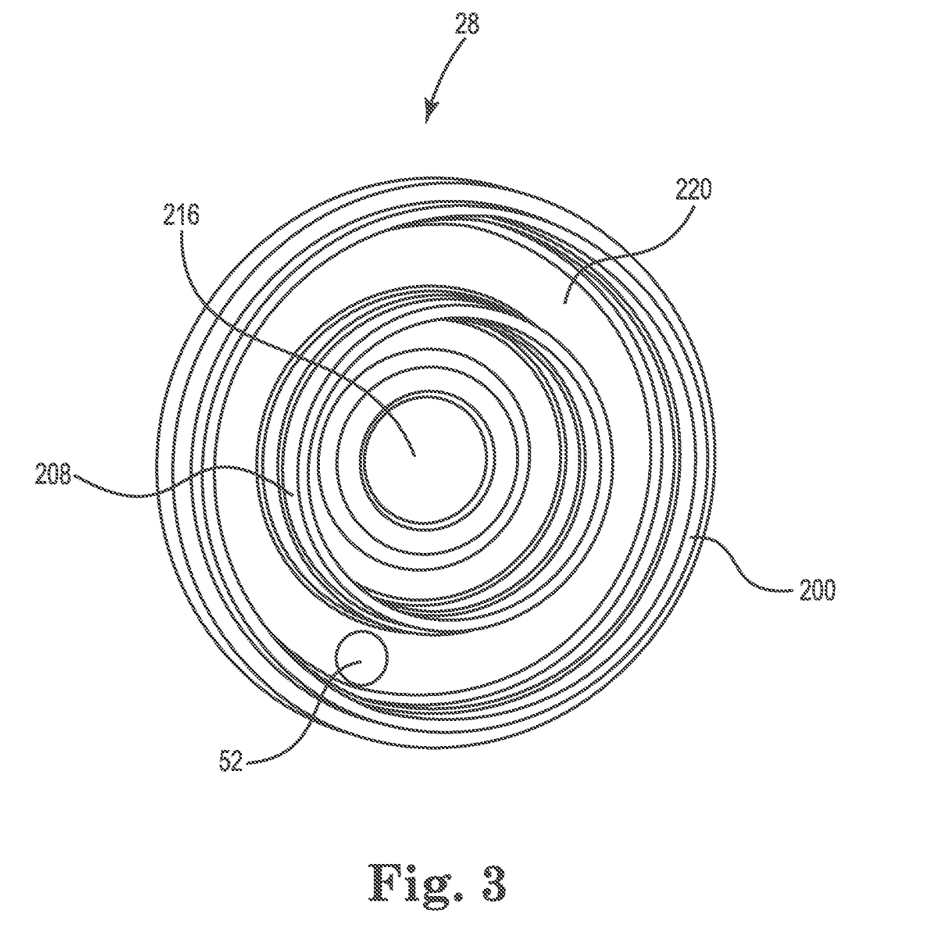
FIG. 3 is a diagram illustrating a first end cap, in accordance with various embodiments of the disclosure.
Figure 4:
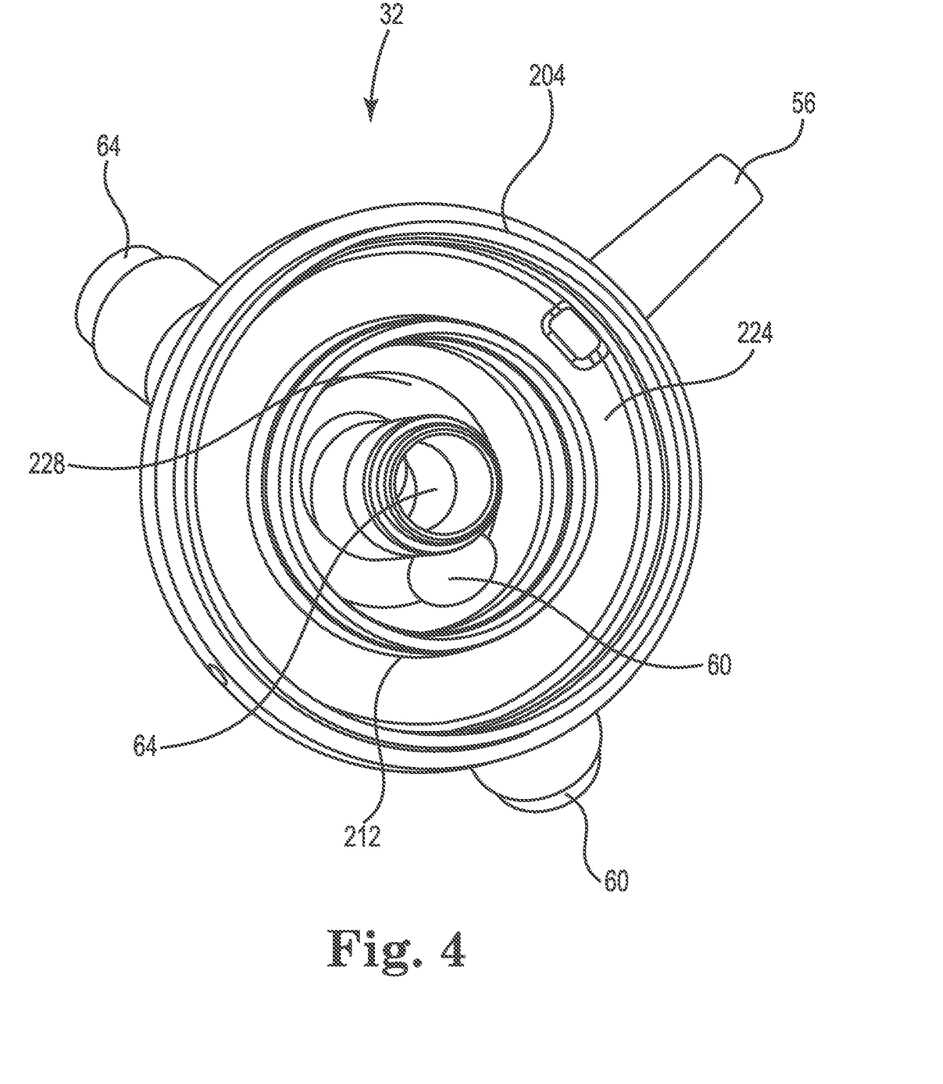
FIG. 4 is a diagram illustrating a second end cap, in accordance with various embodiments of the disclosure.

FIG. 3 and FIG. 4 are diagrams illustrating the first end cap 28 and the second end cap 32, respectively, in accordance with various embodiments of the disclosure. The first end cap 28 and the second end cap 32 are each configured to be secured to the housing 24. The first end cap 28 and/or the second end cap 32 is/are coupled to the housing 24 in any of the various ways including snap-fitting, threading, adhering, and tight-fitting. As shown, the first and second end caps 28, 32 include a first and a second outer annular rings 200, 204, as well as a first and a second inner annular rings 208, 212, respectively. The outer annular rings 200, 204 are disposed about a periphery of the end caps 28, 32 and serves as attachment points for securing the end caps 28, 32 to the housing 24. The inner annular rings 208, 212 are disposed on the end caps 28, 32 and serves as attachment points for securing the end caps 28, 32 to a cylindrical shell 268 (see FIG. 6).

As shown in FIG. 3, the first end cap 28 has a blood inlet aperture 216 where the blood inlet 44 extends into the blood processing apparatus 20. The gas inlet 52 is part of the first end cap 28, where gas is directed into the gas exchanger chamber 76. The gas outlet 56 is integrally formed with the second end cap 32. A gas inlet chamber 220 defined by the first end cap 28 is configured to direct gas from the gas inlet 52 to the gas exchanger chamber 76 of the blood processing apparatus 20.

As shown in FIG. 4, the heat exchanger fluid inlet 60 and the heat exchanger fluid outlet 64 are integrally formed with the second end cap 32. The heat exchanger fluid outlet 64 has a straight section and an angled section, wherein the straight section is concentric with the second end cap 32. A gas outlet chamber 224 defined by the second end cap 32 is configured to direct gas from the blood processing apparatus 20 to the gas outlet 56. The second end cap 32 includes an inlet chamber 228 in fluid communication with the heat exchanger fluid inlet 60 and is configured to direct heat exchanger fluid into the heat exchanger chamber 72. As shown in FIG. 4, the inlet chamber 228 is formed as part of the second end cap 32. In some embodiments, the heat exchanger fluid inlet 60 is located on the second end cap 32 while the heat exchanger fluid outlet 64 is located on one of the first end cap 28 and the second end cap 32.

Figure 5A:
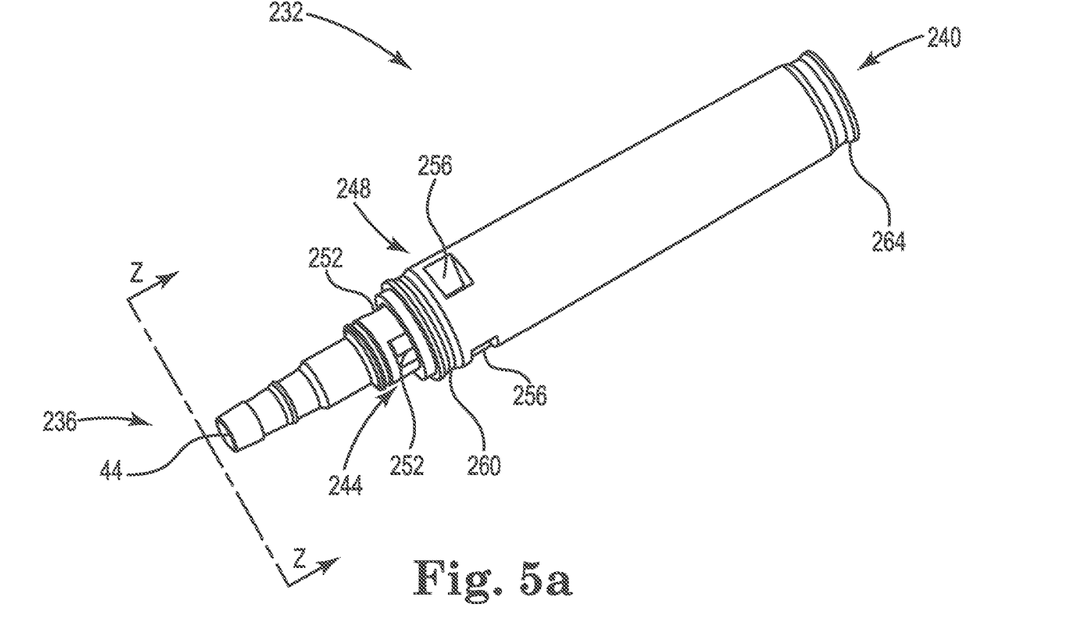
FIG. 5a is a diagram illustrating a heat exchanger core, in accordance with various embodiments of the disclosure.
Figure 5B:
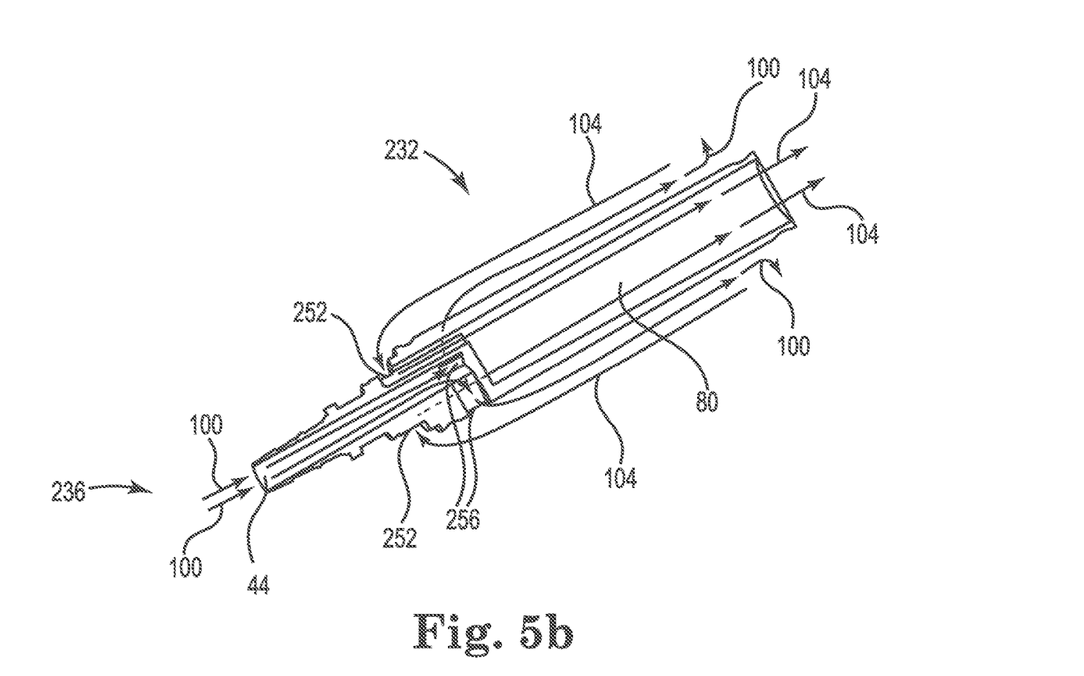
FIG. 5b is a diagram illustrating a heat exchanger core with the blood and fluid flow paths drawn, in accordance with various embodiments of the disclosure.

FIG. 5a is a diagram illustrating the heat exchanger core 232 in accordance with various embodiments of the disclosure. FIG. 5b is a diagram illustrating the flow paths of the blood and the heat exchanger fluid 100, 104 near the heat exchanger core 232. As shown in FIG. 5a, the heat exchanger core 232 has a first core end 236 and a second core end 240. The blood inlet 44 is a portion of the heat exchanger core 232 near the first core end 236. The heat exchanger core 232 includes a fluid flow distributor 244 and a blood flow distributor 248. The fluid flow distributor 244 defines a plurality of fluid flow distributing apertures 252 concentrically positioned on the heat exchanger core 232. The fluid flow distributor 244 is configured to direct heat exchanger fluid from an exterior of the heat exchanger core 232 to the central chamber 80 through the fluid flow distributing apertures 252. The blood flow distributor 248 defines a plurality of blood flow distributing apertures 256 concentrically positioned on the heat exchanger core 232. The blood flow distributor 248 is configured to direct blood from the blood inlet 44 to the exterior of the heat exchanger core 232 through the blood flow distributing apertures 256.

As shown, the fluid flow distributor 244 and the blood distributor 248 are integrally formed as portions of the heat exchanger core 232. In other embodiments, the flow distributors 244, 248 are separate parts, or portions of a multi-flow distributor configured to be coupled to the heat exchanger core 232. The fluid flow distributor 244 and/or the blood flow distributor 248 is/are disposed between 5 to 35 percent of the longitudinal length of the housing 24 from the first end cap 28.

As shown, the heat exchanger core 232 is disposed within the blood processing apparatus 20 such that the first core end 236 is near the first end cap 28 and the second core end 240 is near the second end cap 32. The heat exchanger core 232 includes a first core annular ring 260 configured to help locate the first core end 236 relative to the first end cap 28 guided by the blood inlet aperture 216 on the first end cap 28. The heat exchanger core 232 includes a second core annular ring 264 configured to help locate the second core end 240 relative to the second end cap 32 guided by the heat exchanger fluid outlet 64 on the second end cap 32.

Figure 6:
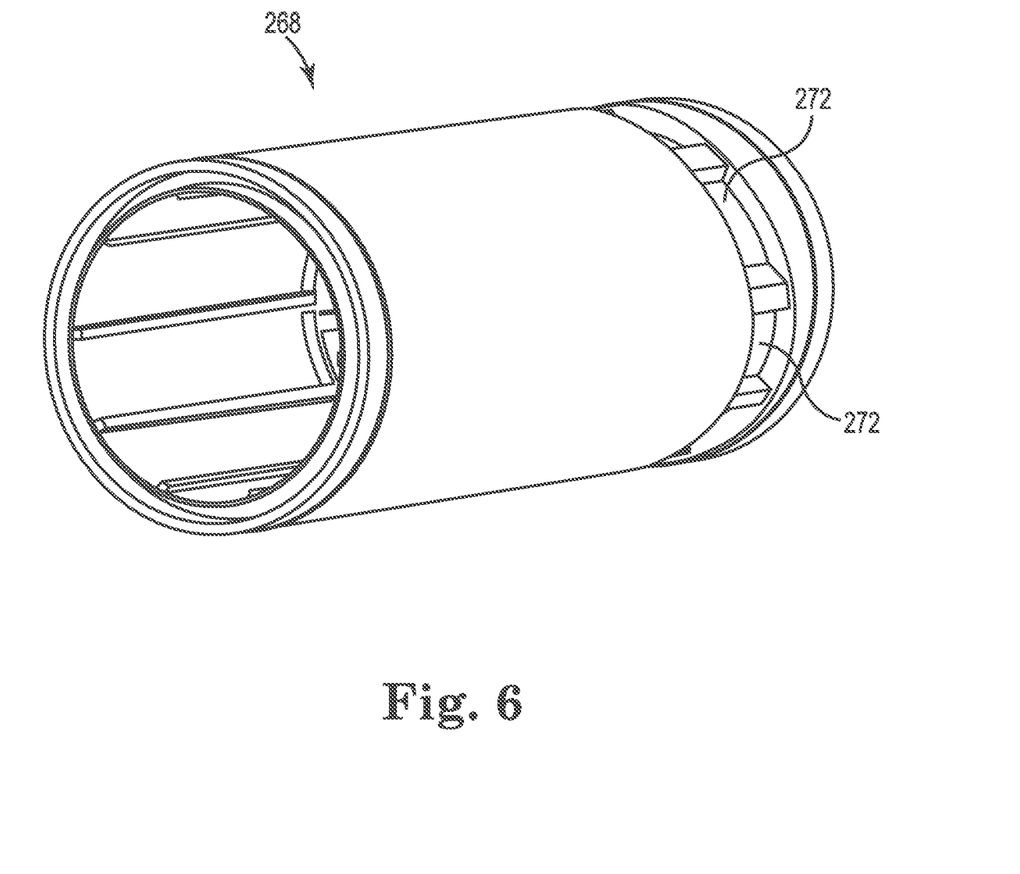
FIG. 6 is a diagram illustrating a cylindrical shell, in accordance with various embodiments of the disclosure.

FIG. 6 is a diagram illustrating a cylindrical shell 268 in accordance with various embodiments of the disclosure. The cylindrical shell 268 is disposed in the housing 24 and arranged coaxially with the heat exchanger core 232. The space between the cylindrical shell 268 and the heat exchanger core 232 defines the heat exchanger chamber 72. The space between the cylindrical shell 268 and the housing 24 defines the gas exchanger chamber 76. The gas inlet chamber 220 includes a gas exchanger element 276 configured for gas to pass from the gas inlet 52 through the gas inlet chamber 220 to the gas exchanger element 276, and to the gas outlet chamber 224, then to the gas outlet 56. The cylindrical shell 268 forms an annular shell aperture 272 configured to allow blood to flow from the heat exchanger chamber 72 to the gas exchanger chamber 76 through the annular shell aperture 272. In some embodiments, the annular shell aperture 272 includes one, two, three, four, five, six or any desired number of apertures spaced radially about the cylindrical shell 268. The annular shell aperture 272 is positioned between 5 to 25 percent of the length of the housing 24 from the second end cap 32.

Figure 7A:
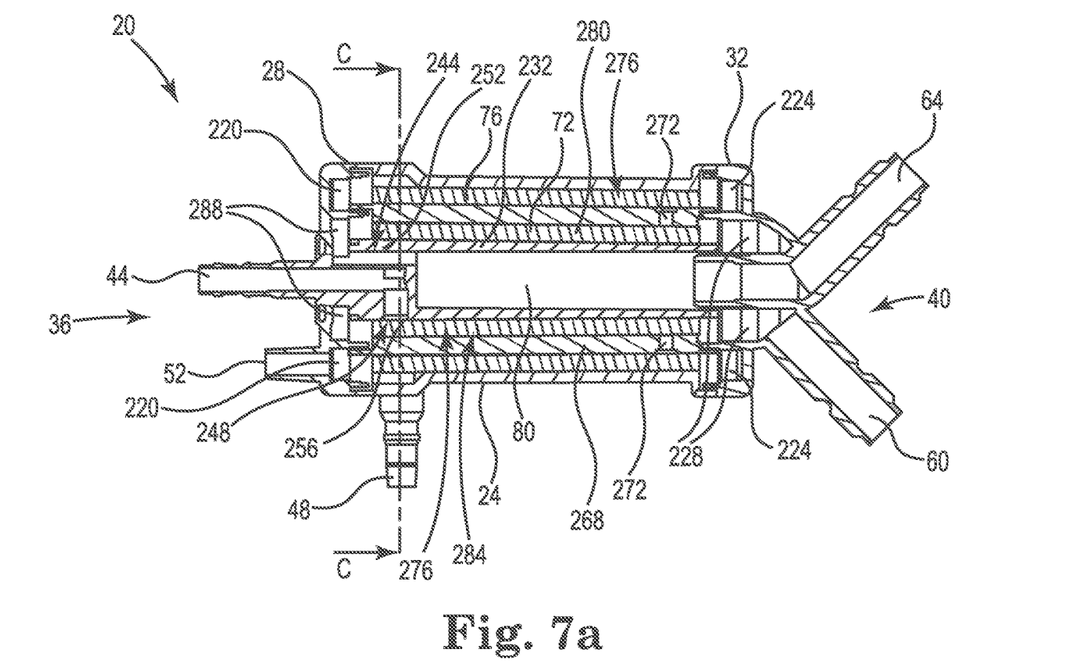
FIG. 7a is a cross-sectional diagram illustrating a blood processing apparatus, in accordance with various embodiments of the disclosure.

FIG. 7a is a cross-sectional diagram illustrating the blood processing apparatus 20 in accordance with various embodiments of the disclosure. The first end cap 28 is attached to the housing 24 near the first end 36, the second end cap 32 is attached to the housing 24 near the second end 40, the heat exchanger core 232 is disposed coaxially in the housing 24, and the cylindrical shell 268 is coaxially positioned in the housing 24 to surround the heat exchanger core 232. The heat exchanger chamber 72 includes a heat exchanger element 280, which in some embodiments, includes one or more heat exchanger hollow fibers 284 in which the heat exchanger fluid flows through from the inlet chamber 228. A post chamber 288 is formed as part of the first end cap 28 configured to direct the heat exchanger fluid from the heat exchanger hollow fibers 284 to the central chamber 80 through the fluid flow distributor 244.

Figure 7B:
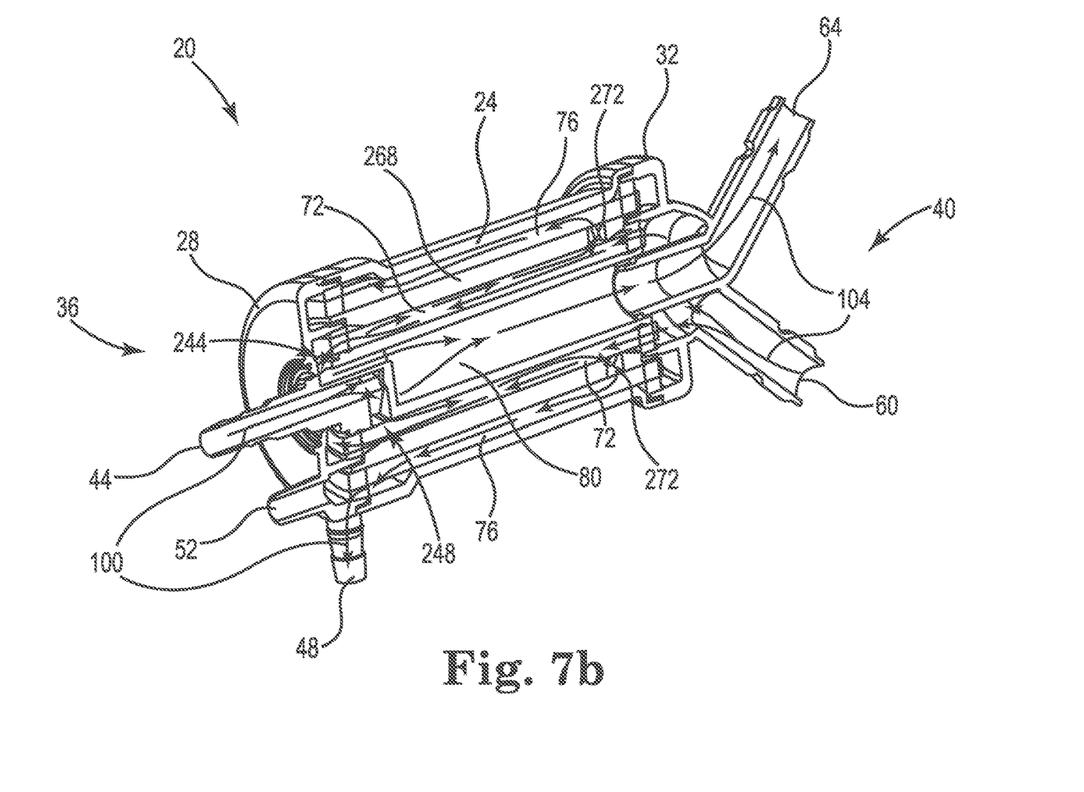
FIG. 7b is a perspective diagram illustrating the blood processing apparatus with the blood and fluid flow paths drawn, in accordance with various embodiments of the disclosure.

FIG. 7b is a diagram illustrating the flow paths of the blood and the heat exchanger fluid 100, 104 in the blood processing apparatus 20 in accordance with various embodiments of the disclosure. As shown, heat exchanger fluid flows from the heat exchanger fluid inlet 60 to the inlet chamber 228 near the second end 40, and through all of the heat exchanger hollow fibers 284 located in the heat exchanger chamber 72 generally from the second end 40 to the first end 36, and into the post chamber 288 near the first end 36, and through the fluid flow distributor 244 to the central chamber 80, and exits the blood processing apparatus 20 through the heat exchanger fluid outlet 64 near the second end 40.

As shown, blood flows from the blood inlet 44 near the first end 36 through the blood flow distributor 248 to the heat exchanger chamber 72 so that blood flows around the heat exchanger hollow fibers 284 generally from the first end 36 to the second end 40 to achieve countercurrent flow. Blood then exits the heat exchanger chamber 72 through the annular shell aperture 272 to the gas exchanger chamber 76, and from the second end 40 back to the first end 36 to exit the blood processing apparatus 20 through the blood outlet 48. Countercurrent flow between the blood and the heat exchanger fluid is realized at least in between the blood flow distributing apertures 256 and the annular shell aperture 272.

The countercurrent flow described above helps accelerate heat exchange between the blood and the heat exchanger fluid as they flow through the heat exchanger chamber. Such accelerated heat exchange improves the responsiveness of temperature regulation of the blood flowing through the blood processing apparatus 20. The rate of heat exchanger is tailored through a wide variety of methods including tuning a flow rate of the blood and/or the heat exchanger fluid, adjusting a temperature of the heat exchanger fluid, modifying a total surface area of the heat exchanger hollow fibers 284 in the heat exchanger chamber 72, arranging the heat exchanger hollow fibers 284 in certain configurations in the heat exchanger chamber 72 to control a degree of at least one of a blood flow resistance and a blood flow turbulence, changing the material choice of the heat exchanger hollow fibers 284 with one of different heat transfer coefficient, and modifying the heat capacity of the heat exchanger fluid.

Figure 8:
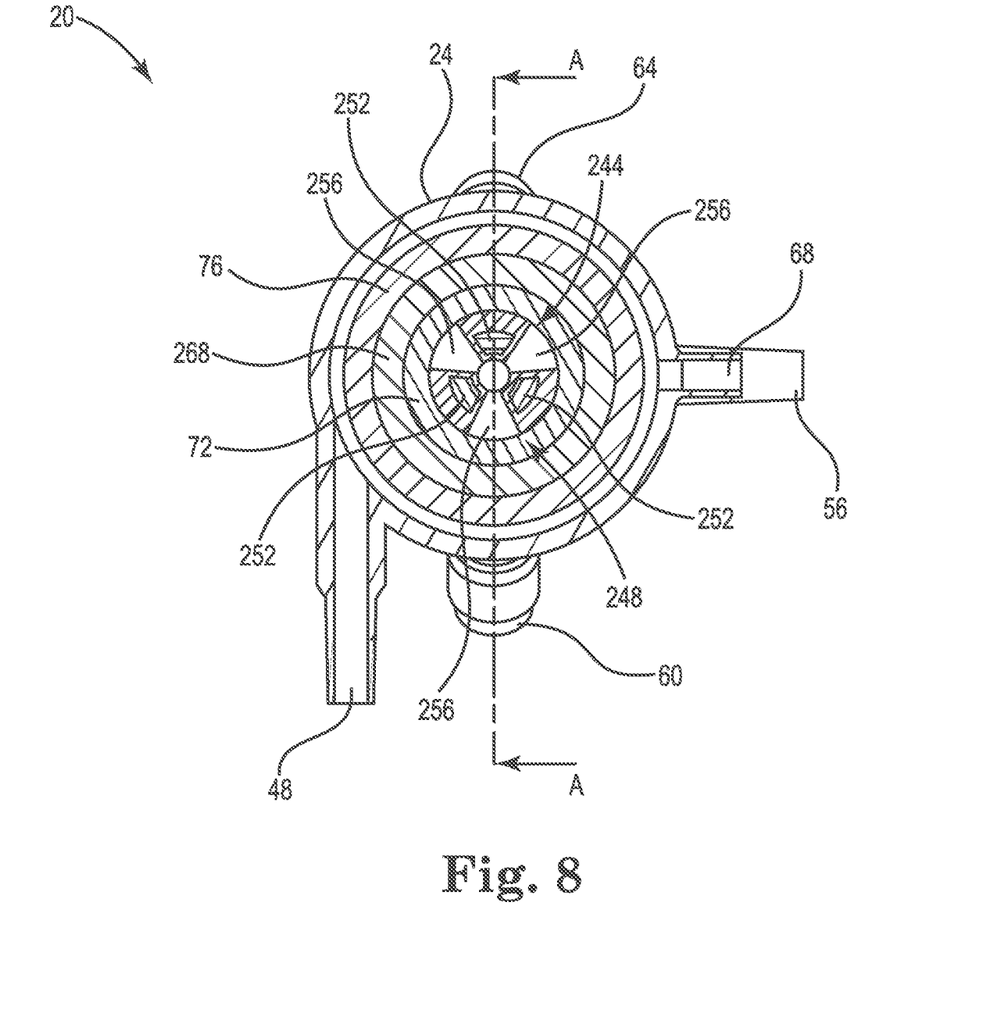
FIG. 8 is a cross-sectional diagram illustrating the blood processing apparatus of FIG. 7a, in accordance with various embodiments of the disclosure.

FIG. 8 is a cross-sectional diagram illustrating the blood processing apparatus 20 in accordance with various embodiments of the disclosure. At least two fluid distributing apertures 252 are radially distributed on the fluid flow distributor 244 for heat exchanger fluid to be directed from the post chamber 288 through the fluid distributing apertures 252 to the central chamber 80. The fluid distributing apertures 252 are equally spaced around the circumference of the fluid flow distributor 244. At least two blood distributing apertures 256 are radially distributed on the blood flow distributor 248 for the blood to be directed from the blood inlet 44 through the blood distributing apertures 256 to the heat exchanger chamber 72. The blood distributing apertures 256 are equally spaced around the circumference of the blood flow distributor 248. In some embodiments, three fluid distributing apertures 252 and three blood distributing apertures 256 are offset radially about the heat exchanger core 232 by 60 degrees, so that the angle between any of the fluid distributing apertures 252 to its nearest neighboring blood distributing aperture is 60 degrees.

Figure 9:
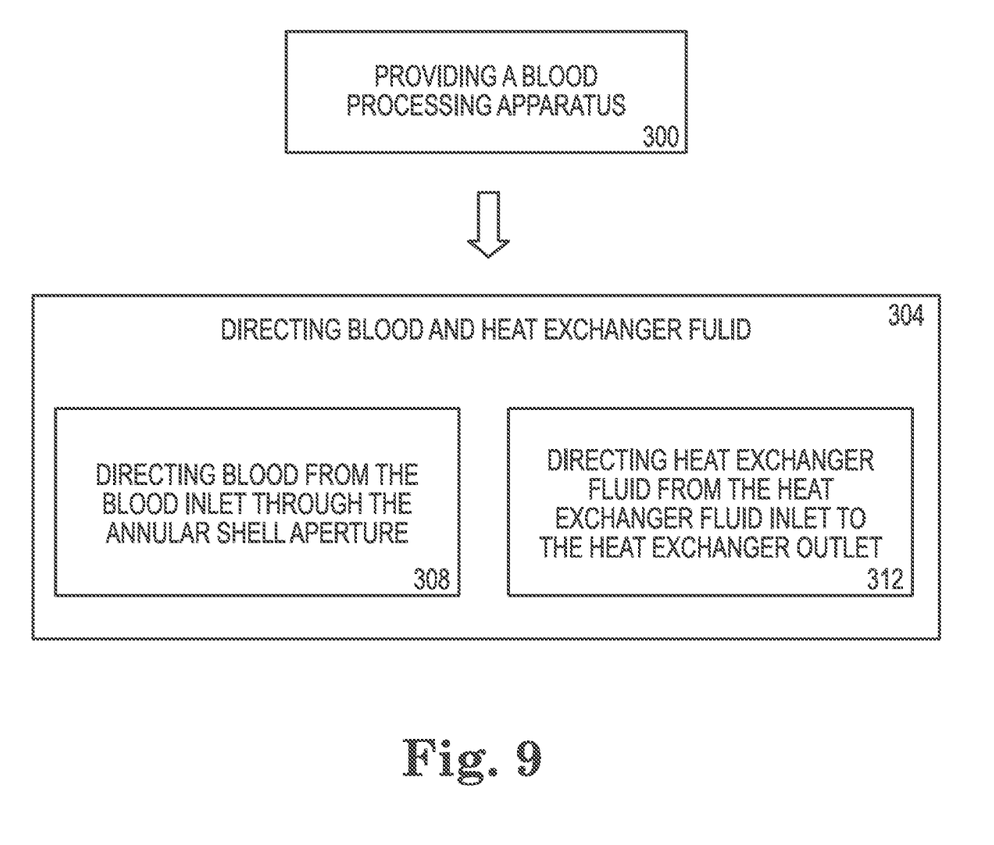
FIG. 9 is a diagram illustrating a method of directing blood and heat exchanger fluid through the blood processing apparatus, in accordance with various embodiments of the disclosure.

FIG. 9 is a diagram illustrating a method of directing blood and heat exchanger fluid through the blood processing apparatus 20 in accordance with various embodiments of the disclosure. In a first step 300, the blood processing apparatus 20 is provided. In a second step 304, blood and heat exchanger fluid are directed through the blood processing apparatus 20. A sub-step of step 2 is directing blood 308, in which blood is directed to flow from the blood inlet 44 through the blood flow distributor 248 to the heat exchanger chamber 72, and through the annular shell aperture 272 to the gas exchanger chamber 76, and exits the blood processing apparatus 20 from the blood outlet 48. Another sub-step of step 2 is directing heat exchanger fluid 312, in which heat exchanger fluid is directed from the heat exchanger fluid inlet 60 to the inlet chamber 228, and to the heat exchanger hollow fibers 284, and into the post chamber 288, and through the fluid flow distributor 244 to the central chamber 80, and exits the blood processing apparatus 20 through the heat exchanger fluid outlet 64.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The following is claimed:

1. A blood processing apparatus comprising:
   a housing having a first end and a second end;
   a blood inlet at the first end;
   a heat exchanger fluid inlet and a heat exchanger fluid outlet at the second end;
   a heat exchanger core situated in the housing;
   a cylindrical shell extending coaxially about the heat exchanger core;
   a blood flow distributor in fluid communication with the blood inlet near the first end and configured to direct blood from the blood inlet at the first end through the blood flow distributor to a heat exchanger chamber, the blood flow distributor defining a plurality of radially distributed blood distributing apertures spaced around a circumference of the blood flow distributor;
   a plurality of heat exchanger hollow fibers disposed in the heat exchanger chamber, the heat exchanger hollow fibers configured to direct heat exchanger fluid from the heat exchanger fluid inlet at the second end through the heat exchanger hollow fibers to a fluid flow distributor near the first end, wherein the fluid flow distributor defines a plurality of radially distributed fluid distributing apertures equally spaced around a circumference of the fluid flow distributor; and
   a central chamber disposed in the heat exchanger core and in fluid communication with the plurality of fluid distributing apertures in the fluid flow distributor, the central chamber configured to direct heat exchanger fluid from the plurality of fluid distributing apertures in the fluid flow distributor near the first end through the central chamber to the heat exchanger fluid outlet at the second end.

2. The blood processing apparatus of claim 1, wherein the heat exchanger chamber is defined by an exterior of the heat exchanger core and an interior of the cylindrical shell.

3. The blood processing apparatus of claim 1, wherein the cylindrical shell further includes an annular shell aperture near the second end and configured to direct blood from the heat exchanger chamber to an exterior of the cylindrical shell.

4. The blood processing apparatus of claim 1, further comprising:
   an inlet chamber in fluid communication with the heat exchanger fluid inlet and the entirety of the heat exchanger hollow fibers near the second end.

5. The blood processing apparatus of claim 1, further comprising:
a post chamber in fluid communication with the entirety of the heat exchanger hollow fibers and the fluid flow distributor near the first end.

6. The blood processing apparatus of claim 1, wherein the blood flow distributor and the fluid flow distributor are portions of a multi-flow distributor.

7. The blood processing apparatus of claim 1, wherein the plurality of radially distributed blood distributing apertures are spaced equally around the circumference of the blood flow distributor.

8. The blood processing apparatus of claim 1, wherein the blood flow distributor is disposed 5 percent to 35 percent of a length of the housing from the first end.

9. The blood processing apparatus of claim 1, wherein the fluid flow distributor is disposed 5 percent to 35 percent of a length of the housing from the first end.

10. The blood processing apparatus of claim 1, wherein the annular shell aperture is disposed 5 percent to 25 percent of a length of the housing apart from the second end.

11. A blood processing apparatus comprising:
a housing having a first end and a second end;
a blood inlet at the first end;
a heat exchanger fluid inlet and a heat exchanger fluid outlet at the second end;
a heat exchanger core situated in the housing;
a cylindrical shell extending coaxially about the heat exchanger core and includes an annular shell aperture near the second end;
a blood flow distributor in fluid communication with the blood inlet near the first end and configured to direct blood from the blood inlet at the first end through the blood flow distributor to a heat exchanger chamber, and through the annular shell aperture to an exterior of the cylindrical shell near the second end, the blood flow distributor defining a plurality of radially distributed blood distributing apertures spaced around a circumference of the blood flow distributor;
a plurality of heat exchanger hollow fibers disposed in the heat exchanger chamber such that heat exchanger fluid flows from the heat exchanger fluid inlet through an inlet chamber to the entirety of the heat exchanger hollow fibers near the second end, and to a post chamber in fluid communication with the entirety of the heat exchanger hollow fibers near the first end; and
a fluid flow distributor in fluid communication with the post chamber, wherein the fluid flow distributor defines a plurality of radially distributed fluid distributing apertures equally spaced around a circumference of the fluid flow distributor.

12. The blood processing apparatus of claim 11, wherein the heat exchanger chamber is defined by an exterior of the heat exchanger core and an interior of the cylindrical shell.

13. The blood processing apparatus of claim 11, further comprising:
a central chamber disposed in the heat exchanger core in fluid communication with the fluid flow distributor, the central chamber configured to direct heat exchanger fluid from the post chamber near the first end through the central chamber to the heat exchanger fluid outlet at the second end.

14. The blood processing apparatus of claim 11, wherein the plurality of radially distributed blood distributing apertures are spaced equally around the circumference of the blood flow distributor.

15. A method of directing blood and heat exchanger fluid through a blood processing apparatus comprising:
providing a blood processing apparatus having:
a housing having a first end and a second end, a blood inlet at the first end, a heat exchanger fluid inlet and a heat exchanger fluid outlet at the second end, a heat exchanger core situated in the housing, a cylindrical shell extending coaxially about the heat exchanger core, the cylindrical shell having an annular shell aperture disposed near the second end, a blood flow distributor in fluid communication with the blood inlet near the first end, a plurality of heat exchanger hollow fibers disposed about an exterior of the heat exchanger core, and disposed in a heat exchange chamber, the blood flow distributor defining a plurality of radially distributed blood distributing apertures spaced around a circumference of the blood flow distributor, and
a central chamber disposed in the heat exchanger core in fluid communication to a fluid flow distributor defining a plurality of radially distributed fluid distributing apertures equally spaced around a circumference of the fluid flow distributor;
directing blood from the blood inlet at the first end through the blood distributing apertures in the blood flow distributor to the exterior of the heat exchanger core in the heat exchange chamber, and through the annular shell aperture near the second end;
and directing heat exchanger fluid from the heat exchanger fluid inlet at the second end through the heat exchanger hollow fibers to the fluid flow distributor near the first end, the fluid flow distributor directing the heat exchanger fluid from an exterior of the heat exchanger core to the central chamber through the fluid distributing apertures and to the heat exchanger fluid outlet at the second end.

16. The method of directing blood and heat exchanger fluid claim 15, further comprising:
directing heat exchanger fluid from the heat exchanger inlet through an inlet chamber to the entirety of the heat exchanger hollow fibers.

17. The method of directing blood and heat exchanger fluid claim 15, further comprising:
directing heat exchanger fluid from the entirety of the heat exchanger hollow fibers through a post chamber to the fluid flow distributor.

* * * * *